United States Patent [19]
Lee et al.

[11] Patent Number: 5,855,826
[45] Date of Patent: Jan. 5, 1999

[54] MATRIX-DOUBLE ENCAPSULATION METHOD AND A COSMETIC COMPOSITION CONTAINING MATRIX-DOUBLE CAPSULES

[75] Inventors: Chung Nam Lee, Koompo; Ok Sob Lee, Anyang; Hak Hae Kang, Seongnam; Dong Soon Park, Yongin, all of Rep. of Korea

[73] Assignee: Pacific Corporation, Seoul, Rep. of Korea

[21] Appl. No.: 769,130

[22] Filed: Dec. 18, 1996

[30] Foreign Application Priority Data

Sep. 17, 1996 [KR] Rep. of Korea .................. 1996-40382

[51] Int. Cl.$^6$ .............................. B01J 13/02; B01J 13/20; B01J 13/22; B01J 13/04
[52] U.S. Cl. ......................... 264/4.32; 264/4.3; 264/4.33; 424/490; 424/493; 428/402; 428/402.21
[58] Field of Search ..................................... 424/401, 489, 424/490, 493; 428/402, 402.21; 264/4.32, 4.3, 4.33

[56] References Cited

U.S. PATENT DOCUMENTS

| | | | |
|---|---|---|---|
| 4,921,757 | 5/1990 | Wheatley et al. | 428/402.2 |
| 5,069,972 | 12/1991 | Versic | 428/402.24 |
| 5,227,298 | 7/1993 | Weber | 435/178 |
| 5,294,446 | 3/1994 | Schlameus et al. | 424/489 |
| 5,401,506 | 3/1995 | Chang et al. | 424/408 |

*Primary Examiner*—Jeffrey C. Mullis
*Attorney, Agent, or Firm*—Foley & Lardner

[57] ABSTRACT

Disclosed herein is a double capsule for cosmetics obtained by matrix-double-encapsulation method which comprises steps of (a) first-encapsulating the fat-soluble active matrials with filming materials to give a microcapsule; (b) encapsulating the microcapsule of the step (a) with gellan gums, and a cosmetic composition containing the same.

5 Claims, No Drawings

MATRIX-DOUBLE ENCAPSULATION METHOD AND A COSMETIC COMPOSITION CONTAINING MATRIX-DOUBLE CAPSULES

BACKGROUND OF THE INVENTION

1. Field of the Invention

The present invention relates to a double capsule for cosmetics and to a cosmetic composition containing it. More particularly, the present invention relates to a double capsule for cosmetics obtained by a matrix-double encapsulation method which comprises steps of (a) first-encapsulating fat-soluble active materials with filming materials to give a microcapsule; and (b) matrix-encapsulating the microcapsule of the step (a) with gellan gums. The present invention can improve the stability of the fat-soluble active materials in the cosmetic base and feel of the cosmetics.

2. Related Arts

The fat-soluble materials are widely used as an active ingredient in cosmetics. The representative examples include retinoids such as retinols, retinoic acids, retinaldehydes and their derivatives; tocopherols; unsaturated fatty acids and their derivatives, fat-soluble pigments, and vitamin F. But they are easily oxidized in air or in aqueous solution, and lose their stability. Especially, although retinol has an outstanding effect in preventing the formation of wrinkles, it has a limit in the use as a cosmetic material due to its instability.

So, in order to incorporate retinol into the cosmetic formulations, it has been used in the form of a water in oil type (W/O type) emulsion. However, in this case, the W/O type emulsion containing retinols tends to be oily and greasy. Additionally, it is unsatisfactory in its stability.

Under this circumstance, many studies have been conducted to provide a method for stabilizing the fat-soluble active materials in cosmetic formulations. For example, the encapsulation method has been introduced in order to stabilize the fat-soluble active materials in the cosmetic formulations.

Usually, the encapsulation techniques for cosmetic materials are divided into the common encapsulation and the matrix encapsulation. In the common encapsulation, active materials as a content are surrounded with filming materials as an outer film. On the other hand, in the matrix encapsulation, active materials are mingled with the filming materials in the series. These encapsulation techniques make it possible to insulate the active materials which have bad compatibility with the cosmetic base within the filming materials, so that their stability in the cosmetics can be improved. Further, the encapsulated active materials can be protected from the outside unfavorable factors and can keep their physicochemical properties until they are applied to the skin. In addition, there is an advantage of ease in handing liquid active materials by encapsulating them. And, there is another advantage of diversifying the function or the effect of the active materials by regulating the particle size and the release speed of the capsule contents.

However, in the common encapsulation techniques, since the filming material is water-soluble and easily swollen in water, water in the cosmetic base may easily penetrate into the capsule or the active ingredient in the capsule may be released. And, when the film of the capsule is hardened or thickened, residues of the film remains onto the skin due to poor pressure-collapse resulting in a poor feel of cosmetic formulations or causing irritation to the skin. Further, in the matrix encapsulation techniques, the active ingredient may be released through the capillaries of the capsule particle.

Under these circumstances, the present inventors have conducted extensive studies in order to provide a new encapsulation technique that allows stabilizing the fat-soluble active material in a cosmetic base without any problems such as soaking water into the capsule, releasing the capsule content into the cosmetic base, or poor feel of cosmetic formulations. As a result, we found that this object can be accomplished by a matrix-double-encapsulation technique.

SUMMARY OF THE INVENTION

Thus, one object of the invention is to provide a matrix-double-encapsulation technique that can stabilize the fat-soluble active materials in a cosmetic composition.

Further, another object of the invention is to provide a matrix-double capsule for cosmetics which can improve the stability of the fat-soluble active materials in the cosmetic composition and feel of the cosmetics.

A third object of the invention is to provide cosmetic compositions containing the matrix-double capsule for cosmetics.

These objects can be accomplished by a matrix-double encapsulation method which comprises steps of (a) first-encapsulating active materials with filming materials to give a microcapsule; and (b) matrix-encapsulating the microcapsule of the step (a) will gellan gums. Further, the cosmetic composition according to the present invention is characterized in that it contains matrix-double capsules obtained by the above matrix-double-encapsulation method.

The other objects and uses of the present invention will become apparent to those skilled in the art by detailed description which will be mentioned below.

DETAILED DESCRIPTION OF THE INVENTION

The matrix-double encapsulation method according to the present invention comprises steps of (a) first-encapsulation and (b) matrix-encapsulation:

wherein said step (a) comprises steps of (a-1) mixing the fat-soluble active materials dispersed in oily materials with an aqueous solution of the filming materials, and then (a-2) cross-linking the filming materials with cross-linking agents to give a microcapsule; and said step (b) comprises steps of (b-1) dispersing the microcapsule into the aqueous solution of gellan gums in an amount of 50% by weight or less to give a dispersion, (b-2) mixing the resulting dispersion with a hydrophobic material such as liquid paraffin, (b-3) adding a resulting mixture to an aqueous solution containing a bivalent ion such as $Ca^{2+}$ in an amount of 0.05~0.2% by weight based on the total weight of composition for the step (b), and (b-4) stirring the resulting mixture at about 100 rpm for 10~30 minutes to give double capsules which is 0.01~2.0 mm in size and in which the microcapsule is fixed in a matrix structure.

In the present invention, fat-soluble active materials are encapsulated by common encapsulation method and matrix encapsulation method continuously. That is, the microcapsule obtained by common encapsulation of step (a) is fixed in matrix structure by matrix encapsulation of step (b). In this regard, common encapsulation of step (a) which is carried out in advance is named "first-encapsulation" and the encapsulation method according to the present invention is named "matrix-double encapsulation method"

In the method according to the present invention, stirring velocity and stirring time are important, since they determine the size of the capsule. As the stirring velocity becomes higher and the stirring time becomes longer, the capsule becomes smaller. Further, the concentration of the bivalent ion such as $Ca^{2+}$ is also important. As the concentration increases, the film becomes harder. Therefore, it is preferable that matrix-encapsulation be carried out in solution containing bivalent ion in an amount of 0.05~0.2% by weight at about 100 rpm for 10~30 minutes.

The present invention will be described in more detail which will be mentioned below.

The fat-soluble active materials for cosmetics contained in the double capsule of the invention may include, but are not limited to, retinoids such as retinols, retinoic acids, retinaldehydes and their derivatives; tocopherols; unsaturated fatty acids and their derivatives; fat-soluble pigments; and vitamin F. The active materials may be used in an amount of 0.1~35% by weight based on the total weight of the capsule.

Also, the oily material for dispersing the active material in the step (a) may include, but are not limited to, mineral oil, squalane, mink oil, octyldodecyl myristic acid, vitamin A, vitamin E, vitamin E fatty acid ester, liquid lanoline, castor oil, olive oil, almond oil, cacao oil, soya oil, fatty alcohol, fatty acid ester and mono-, di- and triglyceride of fatty acid.

Further, the filming materials used in the step (a) may include, but are not limited to, collagen, sodium alginate, agar, gelatin and chitin and its derivatives.

The present invention is characterized in that gellan gums are used as the filming materials in the step (b). Gellan gum is an extracellular anionic polysaccharide produced by the bacterium *Pseudomonas elodea*. It is a partially O-acetylated linear polymer of D-glucose, L-rhamnose, and D-glucuronic acid having the basic repeating unit (excluding acetyl groups)

-3)-β-D-Glcp-(1-4)-β-D-GlcpA-(1-4)-β-D-Glcp-(1-4)-α-L-Rhap-(1- and having 0.5~1.0 million daltons of average molecular weight.

In the conventional matrix encapsulation, collagen, sodium alginate, agar, etc. were employed as the filming material. But, in case of collagen, although it has good solubility in water regardless of pH or ionic concentration, and can be in the form of gel and sol depending on temperature, it may be easily swollen by water in the composition containing the capsule made therefrom and the capsule content may be released into the cosmetic base. Also, in case of sodium alginate, although it has been widely used in hard-encapsulation with polyvalent metal ions, it may leave film residues on the skin due to poor pressure-collapse resulting in a poor feel of cosmetic formulations or causing irritation to the skin. Further, in case of agar, since it can be dissolved only at high temperature and hardened at low temperature, it cannot be used to encapsulate active materials which are unstable to the heat.

Meanwhile, gellan gum has excellent stability to heat and acid and can obtain the same hardness even at a lower concentration than that of collagen, sodium alginate or agar, and so can be employed without the above limitations.

Further, in case of using gellan gum as a filming material, since size of the capsule can be easily controlled, the cosmetics, containing capsule encapsulated with gellan gums can obtain soft feeling and good spreadability even with slight touch. Therefore, gellan gum can be preferably employed as a filming material.

The matrix-double capsule obtained by the above-mentioned encapsulation method is 0.01~2.0 mm in size and has a structure where the microcapsule obtained in a step (a) is fixed in matrix structure. Therefore the active ingredient may be released into the matrix structure through capillaries of the film of the microcapsule without direct exposure to oxygen. Consequently, release of the capsule content into the cosmetic base or penetration of water into the capsule can be prevented and at least be reduced, and so the fat-soluble active materials can be stabilized in the cosmetic base.

As above-described, a double capsule according to the present invention has good stability, so that it can be employed in any type cosmetic compositions, but it may be preferably dispersed in the cosmetic base having a low viscosity or in the O/W type of W/O type emulsions. Further, the amount of the matrix-double capsule in be incorporated to the composition may be, although it may depend on the type and kind of the cosmetic compositions, 0.01~30% by weight based on the total weight of composition.

PREFERRED EMBODIMENT OF THE INVENTION

The present invention will be described in more detail by way of the following examples. However, these examples are provided only for illustration purpose and should not be construed as limiting the scope of the invention, which is properly delineated in the accompanying claims.

[Preparation Example 1] First microcapsule

| Materials | Amount(g) |
|---|---|
| 1. Distilled water | 61.5 |
| 2. Acid(Citric acid, Lactic acid) | q.s. |
| 3. Collagen | 0.5 |
| 4. Glycosaminoglycan | 0.5 |
| 5. BHT | 0.1 |
| 6. Tocopherol | 0.1 |
| 7. Mineral oil | 12 |
| 8. Soya oil | 25 |
| 9. Vitamin A (retinol) | 0.28 |
| 10. Potassium hydroxide | q.s |
| 11. Distilled water | 50 |
| 12. Xanthin gum | 0.5 |
| 13. Butylene glycol | 15 |
| 14. Preservative | q.s. |

Materials 1–9 were mixed in a beaker. At this time, pH of a mixture was controlled to about 3.5 by using material 2. Later, the mixture was neutralized with material 10. After neutralizing completely, the mixture was allowed to stand and the capsules floated. The obtained capsules were washed 2~3 times with distilled water, and then added to the cosmetic base which was prepared in advance by adding materials 12~14 to material 11.

[Preparation Example 2] Matrix-double capsule with gellan gums

| Materials | Amount(g) |
|---|---|
| 1. Distilled water | 19.8 |
| 2. Gellan gum | 0.2 |
| 3. Capsule of preparation example 1 | 25 |
| 4. Liquid paraffin | 20 |
| 5. CaCl$_2$ | 0.2 |
| 6. Distilled water | to 350 |

Material 2 was added to material 1 and then heated up to 70° C. After dissolving, the mixture was cooled to room temperature. Then, after adding material 3 to the mixture, the resulting mixture was added to material 4 and mixed properly. This mixture was added to the solution which was prepared in advance by adding material 5 to material 6, and stirred at about 100 rpm for 10~30 minutes. After stirring and material 4 was separated from the mixture, and the matrix-double capsule was obtained by washing the mixture with distilled water.

[Preparation Example 3] Double capsule with gelatin

| Materials | Amount(g) |
|---|---|
| 1. Distilled water | 12.0 |
| 2. Gelatin | 1.25 |
| 3. Capsule of preparation example 1 | 25 |
| 4. Acetic acid | 4 |
| 5. Formaldehyde(37%) | 4 |
| 6. Distilled water | to 350 |

Material 2 was added to material 1 and heated up to 90° C. After dispersing, the mixture was adjusted to pH 5~6 at 70° C. To this mixture, material 3~6 were added. At this time, pH of the mixture was controlled to about 4.4~4.5 by using material 4. And then, the mixture was cooled to 30° C. Cross-linking was determined visually and then the mixture was cooled to 5° C. and adjusted to pH 2.0. Material 5 was added to the resulting mixture and stirred for 12~24 hours. After stirring, gelatin double capsule was obtained by filtration.

[Experimental Example 1] Activity of Retinol

In order to evaluate the stability of retinol in the cosmetic base, the test samples containing retinol 3,000 IU were prepared by dispersing the following samples in the following base in a ratio of 1:1.

| | |
|---|---|
| Sample 1 | 6,000 IU of retinol solution with absolute ethanol |
| Sample 2 | 6,000 IU of capsule of preparation 1 |
| Sample 3 | 6,000 IU of capsule of preparation 2 |
| Sample 4 | 6,000 IU of capsule of preparation 3 |
| herein, IU = 0.3 μg of retinol) | |

[Base]

| | |
|---|---|
| distilled water | 37.0 g |
| concentrated glycerin | 10.0 g |
| polyoxyethylene (20) sorbitan monostearate | 3.0 g |

$$\text{Activity of retinol} = \frac{\text{g of sample 1} \times \text{absorbance sample of sample} \times \text{activity of sample 1}}{\text{g of sample} \times \text{absorbance of sample 1}}$$

Air was blown to the test samples under stirring at 30° C. for 24 hours. The activity of retinol was calculated by following the formula given above and using the absorbance of the samples measured with the UV-Visible Spectrophotometer(Cary 1E of Varian Co.). Activity was measured twice in the samples as soon as they were prepared and in the test materials after 24 hours' blowing. The results are shown in Table 1.

TABLE 1

| | Sample 2 | | Sample 3 | | Sample 4 | |
|---|---|---|---|---|---|---|
| | Instantly | 24 hours later | Instantly | 24 hours later | Instantly | 24 hours later |
| Activity (IU) | 5726.43 | 2339.36 | 5799.21 | 2850.66 | 4505.97 | 2097.47 |
| Efficiency (%) | 95.44 | 77.98 | 96.98 | 95.02 | 75.10 | 69.92 |

As shown in Table 1, the activity of retinol was maintained exceeding to 95% by matrix-double encapsulation (preparation example 2). That is to say, the fat-soluble active materials can be stabilized by matrix-double encapsulation.

[Example 1 and Comparative Examples 1 and 3]

| | | Comparative Examples | | |
|---|---|---|---|---|
| Materials | Example 1 | 1 | 2 | 3 |
| 1. Stearic acid | 1.0 | 1.0 | 1.0 | 1.0 |
| 2. Cetostearyl alcohol | 0.7 | 0.7 | 0.7 | 0.7 |
| 3. Microcrystalline wax | 0.2 | 0.2 | 0.2 | 0.2 |
| 4. Glyceryl monosterate | 0.5 | 0.5 | 0.5 | 0.5 |
| 5. Liquid paraffin | 5.0 | 5.0 | 5.0 | 5.0 |
| 6. Sorbitanmonostearate | 0.3 | 0.3 | 0.3 | 0.3 |
| 7. Polyxyethylene sorbitan monostearate | 1.1 | 1.1 | 1.1 | 1.1 |
| 8. Squalane | 3.5 | 3.5 | 3.5 | 3.5 |
| 9. Dimenthicone | 0.5 | 0.5 | 0.5 | 0.5 |
| 10. Distilled water | to 100 | to 100 | to 100 | to 100 |
| 11. Concentrated glycerine | 6.5 | 6.5 | 6.5 | 6.5 |
| 12. Carboxyvinyl polymer | 0.12 | 0.12 | 0.12 | 0.12 |
| 13. Hyaluronic acid extract | 0.5 | 0.5 | 0.5 | 0.5 |
| 14. Xanthin gum | 0.02 | 0.02 | 0.02 | 0.02 |
| 15. Preservative | q.s. | q.s. | q.s. | q.s. |
| 16. Perfume | q.s. | q.s. | q.s. | q.s. |
| 17. Capsule of preparation 2 | 6.0 | — | — | — |
| 18. Retinol solution | — | 0.1 | — | — |
| 19. Capsule of preparation 1 | — | — | 3.0 | — |
| 20. Capsule of preparation 3 | — | — | — | 6.0 |

Materials 1~9 and materials 10~15 were separately mixed and heated up to 73° C. The two mixtures were mixed together and material 18 was added thereto. After emulsifying at about 3600 rpm for 3 minutes, the mixture was cooled to room temperature and material 17 was added thereto and stirred. Retinol content contained in these examples corresponds to 3,000 IU.

[Experimental Example 2]

In order to evaluate the stability of retinol in the cosmetic compositions, the activities of retinol of cosmetics obtained in Example 1 and Comparative Examples 1~3 were measured by the same method as that of Experimental example 1. The results are shown in Table 2.

TABLE 2

(Being stored at 45° C.)

|  | Example 1 | | Comparative Examples | | | | | |
|---|---|---|---|---|---|---|---|---|
|  | | | 1 | | 2 | | 3 | |
|  | Instantly | 1 month later | Instantly | 1 month later | Instantly | 1 month later | Instantly | 1 month later |
| Activity (IU) | 2880.6 | 2769.9 | 2427.3 | 558.3 | 2784.9 | 1889.4 | 2048.1 | 1792.5 |
| Efficiency (%) | 96.02 | 92.33 | 80.91 | 18.61 | 92.83 | 62.98 | 68.27 | 59.75 |

As shown in Table 2, it was understood that activity of retinol is maintained at greater than 90% even after the cosmetics containing matrix-double capsule of retinol (Example 1) was stored at about 45° C. for one(1) month.

[Experimental Example 3] Stability of the Cosmetics

In order to evaluate the stability of the cosmetics obtained in Example 1 and Comparative Examples 1~3, the cosmetics were stored for one(1) month at the following temperatures, and observed for instability such as phase separation, discoloration and odorizing.

Especially, cycling test was carried out in cycling chamber of which the temperature is set −20° C. and 37° C. Temperature of the chamber was changed from −20° C. to 37° C. and then from 37° C. to −20° C. every 24 hours, and cycling was performed 3~7 times.

The results are shown in Table 3.

TABLE 3

|  | Example 1 | Comparative Examples | | |
|---|---|---|---|---|
|  |  | 1 | 2 | 3 |
| Room temperature | stable | unstable | stable | stable |
| 45° C. | stable | unstable | unstable | unstable |
| After 4 times cycling | stable (stable even after 7 times cycling) | unstable | unstable | unstable |
| Discoloration (after storage at 45° C. for 1 month) | not observed | severe discoloration | a little discoloration | a little discoloration |
| Odorizing (after storage at 45° C. for 1 month) | not observed | severe odorizing (bad smell) | a little odorizing | a little odorizing |

[Experimental Example 4]

In order to evaluate the effect of the cosmetic composition containing the matrix-double capsule according to the present invention on the skin, a panel test was carried out. 100 males and females aged 20~40 years used the cosmetics of Example 1 and Comparative Examples 2~3 and evaluated feel on the skin according to the following scoring system. The results are average score and shown in Table 4.

1: Extremely rough feeling; much film residue
2: Slightly rough feeling, a little film residue
3: Initially rough feeling but smooth presently soon; no film residue
4: Initially smooth feeling, no film residue

TABLE 4

| Test materials | Example 1 | Comparative Examples | |
|---|---|---|---|
|  |  | 2 | 3 |
| Average score | 3.53 | 2.48 | 2.27 |

As shown in Tables 3 and 4, it is understood that the cosmetic composition containing the matrix-double capsule of retinol has good stability to change of temperature and good feel, compared with the cosmetic compositions containing common capsule.

EFFECT OF THE INVENTION

As shown by the above description, the stability of the fat-soluble active materials and feel of the cosmetic compositions containing capsules of these active materials can be improved by matrix-double encapsulation method.

What is claimed is:

1. A cosmetic composition comprising a double capsule, which composition is obtained by an encapsulation method comprising microencapsulating fat-soluble active materials with a filming material selected from the group consisting of collagen, sodium alginate, agar, gelatin and chitin and its derivatives to produce microcapsules, and then encapsulating the microcapsules in a matrix of gellan gums.

2. The cosmetic composition according to claim 1, wherein the fat soluble active material is selected from the group consisting of retinols, retinoic acids, retinaldehydes and their derivatives; tocopherols; unsaturated fatty acids and their derivatives; fat soluble pigments; and vitamin F.

3. The cosmetic composition according to claim 1, which comprises a double capsule in an amount of 0.01–30% by weight based on a total weight of the composition.

4. An encapsulation method comprising:
   (a) microencapsulating a fat-soluble active material with a filming material selected from the group consisting of collagen, sodium alginate, agar, gelatin and chitin and its derivatives to produce microcapsules, and then
   (b) encapsulating the microcapsules in a matrix of gellan gums to produce a cosmetic composition as claimed in claim 1.

5. An encapsulation method according to claim 4, wherein the fat soluble active material is selected from the group consisting of retinols, retinoic acids, retinaldehydes and their derivatives; tocopherols; unsaturated fatty acids and their derivatives; fat soluble pigments; and vitamin F.

* * * * *